United States Patent [19]
Hill

[11] Patent Number: 5,993,784
[45] Date of Patent: Nov. 30, 1999

[54] LOW FOAMING THERAPEUTIC TOOTHPASTES WITH IMPROVED CLEANING AND ABRASION PERFORMANCE

[75] Inventor: Ira D. Hill, Locust, N.J.

[73] Assignee: WhiteHill Oral Technologies, Locust, N.J.

[21] Appl. No.: 08/899,558

[22] Filed: Jul. 24, 1997

[51] Int. Cl.⁶ ............... A61K 7/16; A61K 7/18; A61K 7/22
[52] U.S. Cl. ............... 424/49; 426/52; 426/54
[58] Field of Search ........... 424/49–88; 15/207.2

[56] References Cited

U.S. PATENT DOCUMENTS

| | | | |
|---|---|---|---|
| 1,773,969 | 4/1930 | Dreyfus et al. | 15/207.2 |
| 2,207,157 | 7/1940 | Neville | 15/207.2 |
| 2,317,485 | 4/1943 | Rider | 15/207.2 |
| 2,433,325 | 12/1947 | Slaughter | 15/207.2 |
| 2,434,533 | 1/1948 | Wurzburger | 15/207.2 |
| 2,443,055 | 6/1948 | Reis | 15/207.2 |
| 2,508,799 | 5/1950 | Reis | 15/207.2 |
| 2,637,893 | 5/1953 | Shaw | 15/207.2 |
| 2,666,976 | 1/1954 | Olmer et al. | 15/207.2 |
| 3,121,040 | 2/1964 | Shaw et al. | 15/207.2 |
| 3,124,823 | 3/1964 | Charvat | 15/207.2 |
| 3,186,018 | 6/1965 | Shaw | 15/207.2 |
| 3,344,457 | 10/1967 | Grobert | 15/207.2 |
| 3,383,276 | 5/1968 | Gould | 15/207.2 |
| 3,411,979 | 11/1968 | Lewis | 15/207.2 |
| 3,505,163 | 4/1970 | Meers et al. | 15/207.2 |
| 3,605,162 | 9/1971 | Long | 15/207.2 |
| 4,307,478 | 12/1981 | Ward et al. | 15/207.2 |
| 4,559,268 | 12/1985 | Nakashima et al. | 428/397 |
| 4,623,536 | 11/1986 | Winston et al. | 424/49 |
| 4,663,153 | 5/1987 | Winston et al. | 424/52 |
| 4,687,663 | 8/1987 | Schaeffer | 424/52 |
| 4,721,614 | 1/1988 | Winston et al. | 424/52 |
| 4,806,339 | 2/1989 | Parran, Jr. et al. | 424/52 |
| 4,806,340 | 2/1989 | Gaffar et al. | 424/52 |
| 4,812,308 | 3/1989 | Winston et al. | 424/52 |
| 4,837,008 | 6/1989 | Rudy et al. | 424/53 |
| 4,842,165 | 6/1989 | Van Coney | 222/95 |
| 4,849,213 | 7/1989 | Schaeffer | 424/53 |
| 4,867,988 | 9/1989 | Chernack | 424/490 |
| 4,885,155 | 12/1989 | Parran, Jr. et al. | 424/52 |
| 4,889,712 | 12/1989 | Gaffar et al. | 424/52 |
| 4,891,211 | 1/1990 | Winston | 424/52 |
| 4,897,258 | 1/1990 | Rudy et al. | 424/53 |
| 4,925,655 | 5/1990 | Smigel et al. | 424/52 |
| 4,943,429 | 7/1990 | Winston et al. | 424/52 |
| 4,956,237 | 9/1990 | Samuelson | 428/398 |
| 4,971,782 | 11/1990 | Rudy et al. | 424/53 |
| 4,980,152 | 12/1990 | Frazier et al. | 424/52 |
| 4,999,184 | 3/1991 | Parran, Jr. et al. | 424/52 |
| 5,000,941 | 3/1991 | Chernack | 424/49 |
| 5,004,597 | 4/1991 | Majeti et al. | 424/52 |
| 5,009,881 | 4/1991 | Hill et al. | 424/49 |
| 5,041,280 | 8/1991 | Smigel | 424/52 |
| 5,085,853 | 2/1992 | Williams et al. | 424/53 |
| 5,180,576 | 1/1993 | Winston et al. | 424/52 |
| 5,256,402 | 10/1993 | Prencipe et al. | 424/53 |
| 5,374,368 | 12/1994 | Hauschild | 252/95 |
| 5,424,060 | 6/1995 | Hauschild | 424/52 |
| 5,701,629 | 12/1997 | O'Brien | 15/207.2 |

*Primary Examiner*—Shep K. Rose
*Attorney, Agent, or Firm*—Ernest V. Linek; Banner & Witcoff, Ltd.

[57] ABSTRACT

Low foaming therapeutic toothpastes containing a therapeutic substance, an abrasive, a humectant, a low foam surfactant, and/or a foam control agent having improved cleaning and abrasion performance wherein: packing of the abrasive into the channels of a channeled bristle toothbrush, and abrasive/tooth surface contact, are substantially free from surfactant bubble interference such that Cleaning Efficiency Coefficient and Abrasion Efficiency Coefficient values greater than about 1.1 are achieved along with improvements in therapeutic efficacy.

11 Claims, 2 Drawing Sheets

LOW FOAMING THERAPEUTIC TOOTHPASTES WITH IMPROVED CLEANING AND ABRASION PERFORMANCE

FIELD OF THE INVENTION

Low foaming therapeutic toothpastes containing a therapeutic substance, an abrasive, a humectant, a low foam surfactant, and/or a foam control agent having improved cleaning and abrasion performance wherein: packing of the abrasive into the channels of a channeled bristle toothbrush, and abrasive/tooth surface contact, are substantially free from surfactant bubble interference such that Cleaning Efficiency Coefficient and Abrasion Efficiency Coefficient values greater than about 1.1 are achieved along with improvements in therapeutic efficacy.

BACKGROUND OF THE INVENTION

The present invention relates to therapeutic toothpastes having improved cleaning and abrasion performance attributed to a low foam characteristic and the absence of substantial surfactant bubble interference with the abrasive/tooth surface interface during brushing. As a result of this improved cleaning and abrasion, the therapeutic activity of each of these low foaming toothpastes is generally improved.

In the oral hygiene field today, toothbrushing is generally carried out with a toothbrush/toothpaste combination where the abrasive in the toothpaste is brought into contact with tooth surfaces by the bristles of the toothbrush. The leading commercial toothpastes presently marketed are characterized by a controlled foam profile, resulting in foam initially filling a good part of the oral cavity, eventually dissipating at the end of the brushing cycle, such that the residue can be conveniently expectorated.

Examples of therapeutic toothpastes include "fluoride", "anti-tartar", "anti-plaque", "baking soda", "anti-gingivitis", and "hypersensitivity treatment" toothpastes, some of which are described in the following U.S. Pat. Nos. 4,254,101; 4,515,772; 4,684,518; 4,806,339; 4,806,340; 4,842,165; 4,885,155; 4,889,712; 4,891,211; 4,999,184; 5,004,597; 5,180,576; 5,374,368; and 5,424,060. These patents are to be incorporated by reference in the present specification. The toothpastes described in these patents generally use one or more abrasive substances to abrasively clean, polish and remove stains, plaque and tartar from the surfaces of teeth in preparation for imparting various therapeutic benefits to the oral cavity.

The current level of gum disease and tooth loss attributed to gum disease and gum retraction in adults, along with high incidence of gingivitis, coronal caries and hypersensitivity among adults, suggests the referenced toothpastes may not be cleaning as efficiently as one would hope they would and therefore not imparting the optimum therapeutic benefits intended.

During toothbrushing, the primary function of the toothbrush bristles is to rub abrasive particles contained in the toothpaste across the surfaces of the teeth, thereby removing by abrasive action tooth deposits such as pellicle, stains, plaque, tartar and the like while delivering various active ingredients such as fluoride, anti-tartar, anti-gingivitis ingredients, etc. to the "cleaned" oral cavity.

Studies show that the most aggressive mechanical cleansing with a toothpaste/toothbrush combination should be directed toward the tooth surface, with much less so toward the gingival surface and essentially none toward the base of the gingival sulcus. The basis for these observations is as follows:

1. The development of gingival inflammation and dental caries is most frequently caused by failure to remove dental plaque from the subgingival surface of the tooth and to a much lesser extent materia alba from the gingival surface in the subgingival space. Both dental plaque and materia alba can form within several hours of brushing and therefore frequent mechanical cleansing is essential. Materia alba which consists primarily of an acquired bacterial coating and desquamated epithelial cells, leukocytes and a mixture of salivary proteins and lipids is a soft sticky deposit less adherent than dental plaque. It can be flushed away with a water spray but more completely removed from the gingiva with a mild mechanical cleansing.

2. Dental plaque is formed by oral microorganisms that synthesize harmful products that are destructive to the tooth and gums when not removed from the gingival sulcus. The toxins formed by these microorganisms cause cellular damage to the gingiva with subsequent inflammation (gingivitis) and eventually destruction of the supporting structures (periodontitis). When gingivitis occurs, vascular dilation, capillary proliferation, engorged vessels and sluggish venous return causes a stretched and thinned epithelium that is sensitive to mechanical trauma such as aggressive brushing.

3. Dental plaque with associated gingivitis also causes exposure of the root surface (recession) with increased occurrence of cavities (dental caries). Exposure of the root surfaces can also occur due to faulty brushing by repeated direct trauma to the base of the sulcus (gingival abrasion). When a pathologically deepened gingival sulcus (periodontal pocket) occurs, the pathological condition may become exacerbated because plaque can more readily occur. If dental plaque is not removed, calculus (tartar) is formed by mineralization of the bacterial plaque. Calculus can form within several hours of plaque formation. Calculus has a bacterial plaque coating and exacerbates gingivitis and gingival recession by both chemical irritation from the formed toxins and destruction from the mechanical irritation of the calculus mass. Subgingival calculus usually extends near but does not reach the base of periodontal pockets in chronic periodontal lesions. Calculus holds the plaque against gingiva, and 4. Since materia alba can be removed by light mechanical cleansing and gingival inflammation causes thinning of the gingival epithelium the mechanical cleansing requirement of the gingival surface is much less than the requirement for removing dental plaque from the surface of the teeth.

Accordingly, a more efficient cleansing and abrading therapeutic toothpaste that fulfills the foregoing requirements, and is more effective therapeutically, is desirable.

In order for the abrasives used in toothpastes today to approach optimum cleaning abrasion performance, channeled bristle toothbrushes have been developed to entrap the abrasive and extend abrasive/toothbrush contact beyond tangential contact between bristle tips/abrasive with tooth surfaces. Preferred brushes of this type are described in U.S. application Ser. No. 08/899,679, Attorney Docket No. 1648/46640, filed on even date herewith. The contents of said application are hereby incorporated herein by reference.

In addition to the entrapment of toothpaste abrasive in the channeled bristles, improved toothpaste cleaning efficiency and improved toothpaste abrasion efficiency requires that the abrasive particles entrapped in these bristle channels be brought into direct contact without bubble interference with those tooth surfaces requiring cleaning, polishing, stain removal, etc. This contact is most effective when the bubbles produced by surfactants are minimal and preferably excluded from the abrasive/tooth surface interference.

The use of high foaming surfactants in toothpastes as taught in the referenced patents of market leading toothpastes such as Crest®, Colgate®, Arm & Hammer® . . . although creating the consumer "impression of cleaning" in fact interferes with abrasive packing in bristle channels and with the abrasive/tooth surface contacts required, for optimum cleaning and abrasion performance, similar to the way high foaming detergents interfere with soil removal. Eventually, high foaming detergents gave way to the more efficient low foaming detergents and today have been totally replaced in the laundry market by low foaming (low sudsing) detergents.

The advent of abrasive entrapping toothbrush bristles calls for the use of low foaming surfactants in toothpastes in order to optimize abrasive "packing" in the toothbrush bristles and to optimize abrasive/tooth surface contact during toothbrushing, thereby optimizing toothpaste cleaning and abrasion efficiencies.

Surfactant "bubble" interference with entrapped abrasive/tooth surface contact is illustrated in FIG. 1 of the drawings and is contrasted with substantial bubble free entrapped abrasive/tooth surface contact as is illustrated in FIG. 3. Bubble interference with abrasive packing illustrated in FIG. 2 is contrasted with FIG. 4, which illustrates bubble free abrasive packing in the bristle channel.

OBJECTIVES

The present invention has for its primary objective the enhancement in therapeutic toothpastes of tooth cleaning and polishing through improved toothpaste cleaning and abrasion efficiency wherein improved contact between toothpaste abrasives and tooth surfaces is achieved with a minimum of surfactant bubble interference and with a corresponding improvement in therapeutic results. This improvement in cleaning efficiency is measured by a Cleaning Efficiency Coefficient (CEC). The improvement in abrasion efficiency is measured by an Abrasion Efficiency Coefficient (AEC). Both of these terms are discussed in detail below as are the improvements in various therapeutic effects.

A further objective of the present invention is to enhance the cleaning of those tooth surfaces contiguous to the gingival margin and to the interproximal surfaces while avoiding damaging the soft tissue by using generally lower RDA abrasives, which abrasives are presented to tooth surfaces substantially surfactant bubble free resulting in enhanced CEC and AEC scores.

A further objective of the present invention is to improve the abrasive/tooth surface contact of various commercial therapeutic toothpastes by reducing substantially the sudsing and bubble content of therapeutic toothpastes resulting in improved therapeutic performance. These improved commercial therapeutic toothpastes include low foaming versions of the various toothpastes described in: U.S. Pat. No. 4,254,101; 4,515,772; 4,684,518; 4,806,339; 4,806,340; 4,842,165; 4,885,155; 4,889,712; 4,891,211; 4,999,184; 5,004,597; 5,180,576; 5,374,368; and 5,424,060.

Yet another objective of the invention is to provide an improved method of caring for teeth and gums using a low foaming therapeutic toothpaste with improved CEC and AEC values.

SUMMARY OF THE INVENTION

The foregoing and other objectives, advantages and features are achieved with the present invention through the use of low foaming therapeutic toothpastes whereby the abrasive/tooth surface contact is substantially free from toothpaste surfactant bubbles as shown in FIG. 3 and the Cleaning Efficiency Coefficient (CEC) and Abrasion Efficiency Coefficient (AEC) values of the toothpaste are at least 1.1, with corresponding improvement in therapeutic efficacy.

Improved packing of abrasives into the channels of channeled bristle toothbrushes (which are described in Copending application Ser. No. 08/899,679, supra) is obtained with the low foaming therapeutic toothpastes of the present invention as illustrated in FIG. 4, along with improved efficiency of various therapeutic substances contained in the low foaming toothpastes of the present invention.

Specific embodiments of low foaming toothpastes of the present invention will now be described with reference to the accompanying drawings. In the description that follows, specific low foaming therapeutic toothpaste formulations are described for purposes of clarity, but these are not intended to define or limit the scope of the invention, which is defined in the claims.

DETAILED DESCRIPTION OF THE PREFERRED EMBODIMENTS

For the purposes of the present invention, a low foaming toothpaste is defined as a toothpaste formulation containing an abrasive, a humectant, a surfactant and a foam controlling agent wherein the abrasive/tooth surface interface and abrasive packing in channeled bristle toothbrushes is minimal resulting in CEC and AEC values of at least about 1.1.

For the purposes of the present invention, a therapeutic toothpaste is defined as a toothpaste formulation containing one or more active ingredients for the treatment of oral conditions ranging from chronic plaque and tartar buildup to gingivitis, caries, hypersensitivity, etc.

Figure 1:
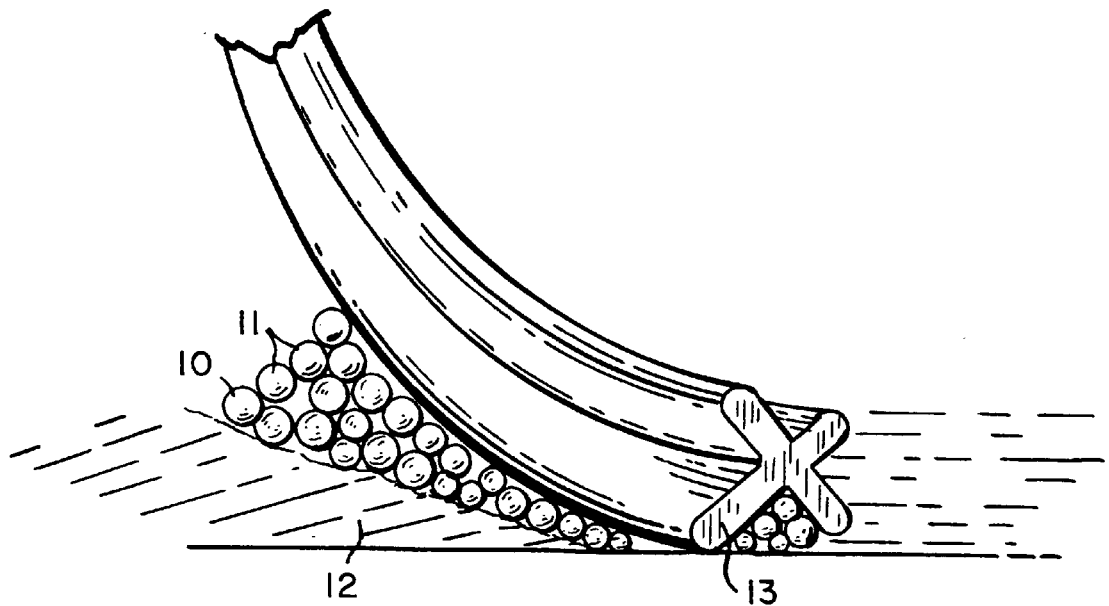
FIG. 1 illustrates schematically the interference of surfactant bubbles with abrasive/tooth surface contact in a channeled bristle toothbrush.
Figure 2A:
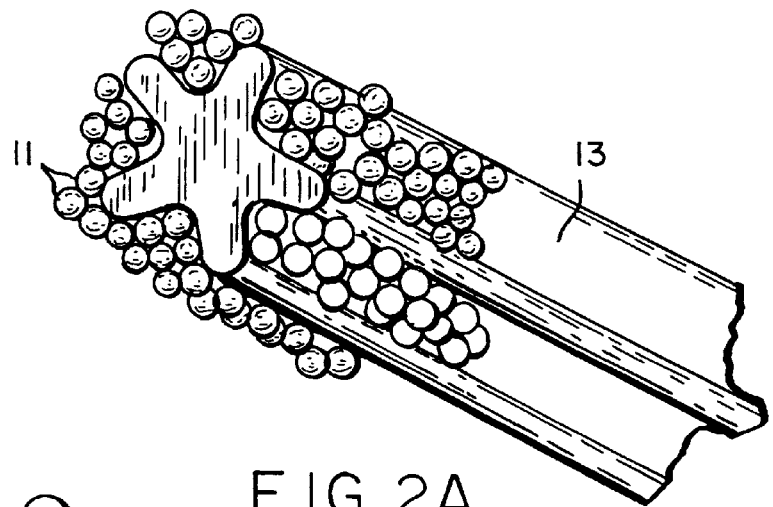
FIG. 2(a) is a cross-sectional view of channeled bristle, 13.
Figure 2B:
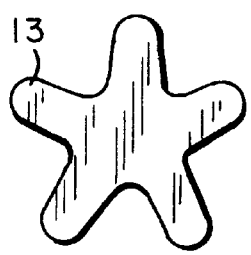
FIG. 2 illustrates schematically the interference of surfactant bubbles with abrasive packing in a channeled bristle toothbrush.
Figure 3:
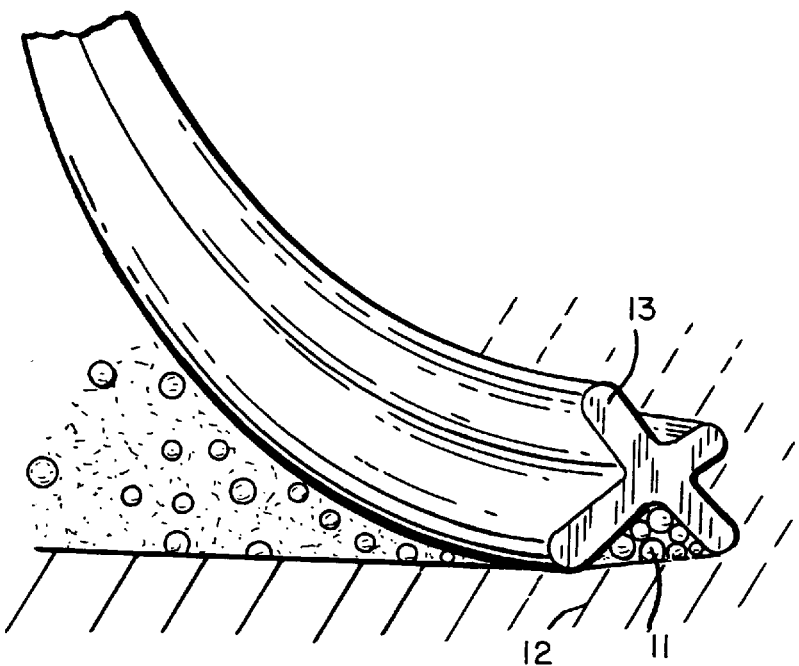
FIG. 3 illustrates schematically the improved abrasive/tooth surface contact achieved with low foaming therapeutic toothpastes of the present invention in a channeled bristle toothbrush.
Figure 4A:
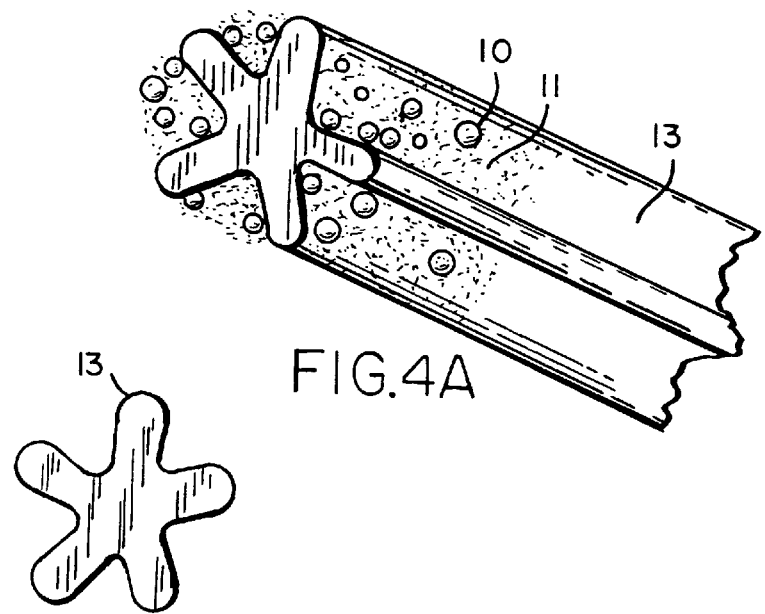
FIG. 4(a) is a cross-sectional view of channeled bristle, 13.
Figure 4B:
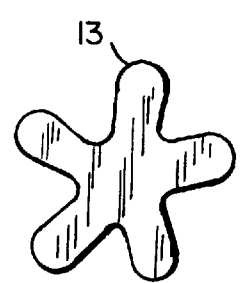
FIG. 4 illustrates schematically the improved abrasive packing in the bristle channels achieved with low foaming therapeutic toothpastes of the present invention.

Referring to FIGS. 1 to 4 of the drawings, the interference of surfactant bubbles (10) with abrasive (11)/tooth surface (12) contact and with abrasive packing in channeled bristle toothbrushes (13) is schematically illustrated. Improved abrasive/tooth surface contact and abrasive packing in the absence of surfactant bubbles is also schematically illustrated in FIGS. 3 and 4.

For the purposes of the present invention, the Cleaning Efficiency Coefficient (CEC) is the cleaning improvement obtained with the low foaming toothpastes of the present invention as measured against a standard foaming toothpaste, with both toothpastes using the same channeled bristle toothbrush.

Specifically, the CEC, is a number that relates the cleaning efficiency of the novel low foaming therapeutic toothpastes of the present invention to a current standard commercial foaming toothpaste, where both toothpastes are tested using identical channeled toothbrushes.

The CEC is a ratio of the efficiency of the low foaming toothpaste to the efficiency of a standard foaming toothpaste under standardized brushing conditions. The ratio is expressed as the reduction in the parameter measured, plaque for example, by the low foaming toothpaste, divided by the reduction in plaque produced by the standard toothpaste under identical toothbrushing test conditions.

This relationship is expressed as:

$$CEC = \frac{\text{Baseline Test} - \text{Final Test}}{\text{Baseline Standard} - \text{Final Standard}}$$

Low foaming therapeutic toothpastes with CEC values above about 1.1, particularly above 1.5, are preferred.

For the purposes of the present invention, Abrasion Efficiency Coefficient (AEC) is defined as the ratio of the results of a standard RDA, Stain Index or Polishing Index procedure of low surfactant toothpaste to the results of an identical procedure using a standard foaming toothpaste with the same bristled toothbrush used in both instances.

This relationship is expresses as:

$$AEC_{RDA} = \frac{\text{Baseline RDA}_{TEST} - \text{Final RDA}_{TEST}}{\text{Baseline RDA}_{Standard} - \text{Final RDA}_{Standard}}$$

$$AEC_{Stn\ Ind} = \frac{\text{Baseline Stn Ind}_{TEST} - \text{Final Stn Ind}_{TEST}}{\text{Baseline Stn Ind}_{Standard} - \text{Final Stn Ind}_{Standard}}$$

$$AEC_{Polish\ Ind} = \frac{\text{Baseline Polish Ind}_{TEST} - \text{Final Polish Ind}_{TEST}}{\text{Baseline Polish Ind}_{Standard} - \text{Final Polish Ind}_{Standard}}$$

For the purposes of the present invention, AEC values for RDA, Stain Index and Polish Index above about 1.1 are preferred with values about 1.5 particularly preferred.

Relative Dental Abrasion (RDA) has long been the standard measurement for predicting the performance of a given toothpaste formulation, and/or the functionality of a series of abrasives having varying particle sizes, compositions of matter, crystal structures, fracture edges, etc. Typically a measured number of strokes with a standard toothbrush with a fixed applied pressure against a piece of dental enamel fixed in a holding plate is the basis of the test. Sometimes a plate of soft metal, such as copper, is substituted for the dental enamel as an inexpensive approximation method. The dental enamel is measured for loss of surface enamel (or metal) by a variety of methods, including weight loss, optical comparison and radioactive techniques.

A similar measurement using artificially stained enamel measures the abrasive removal of stain. In a similar fashion, one can evaluate the polishing of tooth surfaces, a process that increases the reflectance properties of the enamel without a high level of enamel removal or "scratching".

In the present invention, the changing of the toothpaste to a low foaming toothpaste impacts abrasivity whether using RDA, Stain or Polishing measurements. It is suggested that because the delivery of the abrasive to the tooth surface is substantially bubble free and therefore more efficient, certain abrasives will have a higher RDA when used in the low foaming toothpastes of the present invention.

Conversely, if non-scratching abrasives are more efficiently delivered to the tooth surface by the low foaming toothpastes of the present invention, improved cleaning and abrasion results can be produced without resorting to high RDA abrasives and the inherent potential damage they could cause to tooth surfaces, dentin and soft tissue.

The advantage of these low foaming dentifrices is that the teeth are more efficiently cleaned without risking enamel or soft tissue damage that may occur with higher RDA abrasives.

The improved CEC and AEC values obtained with the low foaming therapeutic toothpastes of the present invention result in an improvement in various therapeutic effects ranging from plaque and tartar control to anti-gingivitis and anti-caries effects as well as improved hypersensitivity treatment. Surprisingly, the rate of "tubule" closure is improved with low foaming hypersensitivity treating toothpastes of the present invention.

The low foaming therapeutic toothpaste compositions of the present invention comprise an abrasive, a humectant, a surfactant, a foam control substance, water and an active therapeutic ingredient. Each of these components as well as optional ingredients such as binding agents, flavoring and sweetening substances are described in detail as follows:

ABRASIVE

The therapeutic toothpaste compositions of the present invention contain from between about 1% and about 90%, preferably from between about 10% and 50% by weight, of an abrasive material described in detail below. These abrasives in the low foaming dentifrices of the present invention provide the unique abrasion benefits of exceptionally efficient cleaning, i.e. CEC values above about 1.1 along with exceptional polishing, stain removal and abrasion as indicated by AEC values of at least about 1.1. The exceptional AEC values are obtained without unduly abrading tooth enamel or dentin.

Suitable abrasive materials for the low foaming therapeutic toothpastes of the present invention include: talc, calcium pyrophosphate, calcium hydrogen phosphate dihydrates, anhydrous dicalcium phosphate, calcium carbonate, alumina, tin dioxide, silica, zirconium silicate, sodium bicarbonate, sodium percarbonate, etc., and mixtures thereof. Particularly preferred are abrasive mixtures where the secondary abrasive is the type used in translucent dentifrice gels at levels up to about 20%. Some of these are described in U.S. Pat. No. 3,927,200; 3,906,090, 3,937,321; 3,911,102; 4,036,949; 4,891,211; 4,547,362; 5,374,368; 5,424,060; 5,180,576; 4,943,429; 4,160022; 4,623,536; 4,663,153; and 4,721,614.

Other useful abrasives include: sodium metaphosphate, potassium metaphosphate, magnesium orthophosphate, trimagnesium phosphate, alumina silicate and hetonite as described in U.S. Pat. No. 4,806,340 incorporated herein by reference. See also Thorpe's *Dictionary of Applied Chemistry*, Volume 9, 4th Edition, pp. 510–511.

Particularly preferred abrasives that are compatible with sources of soluble fluoride include those precipitated silica or silica gels such as the silica xerogels described in U.S. Pat. No. 3,538,230 incorporated herein by reference. Preferred are the silica/xerogels marketed under the tradename Syloid by W. R. Erecex Co., Davison Chemical Division.

Especially preferred are the precipitated silica materials such as those marketed by the J. M. Huber Corporation under the tradename Zeodent, particularly the silica carrying the designation Zeodent 119. Other silica dental abrasives useful in the toothpastes of the present invention are disclosed in U.S. Pat. No. 3,862,307 and 4,340,583 incorporated herein by reference.

Other abrasives useful in the low foaming therapeutic dentifrice compositions of the present invention include calcium pyrophosphate including the B-phase calcium pyrophosphate prepared in accordance with the teaching of U.S. Pat. No. 3,112,247 incorporated herein by reference. Another class of abrasives suitable for use with the low foaming toothpastes of the present invention include particulate thermosetting polymerized resins as described in U.S. Pat. No. 3,0750,510 including melamines, phenolics, ureas, melamine-ureas, melamineformaldehydes, urea-formaldehydes, melamine-urea-formaldehydes, cross-linked epoxides and cross linked polyesters. See also U.S. Pat. No. 4,070,510 incorporated herein by reference.

The size of the abrasive particles are most commonly expressed in "mean diameter", i.e. the arithmetical average of the diameters of particles in a representative sample. The mean diameter value of abrasive particles is usually described in microns. Abrasives having particle sizes between about 3 and 25 microns and preferably between about 6 and about 20 microns are particularly preferred for the channel designs of the toothbrush bristles of the present invention.

The preparation of suitable particle size abrasives can be accomplished by conventional techniques well known to the art. Basically, these techniques involve milling various abrasive materials, followed by standard screen sieving (or air separation) to segregate the desired particle size range. Other techniques employ crystallization or related techniques to control size and crystal variants.

SURFACTANT

Organic surface active substances are used in the low foaming therapeutic toothpastes of the present invention to achieve increased cleaning action, assist in complete dispersion of various active ingredients throughout the oral cavity, optimize therapeutic activity, etc. Organic synthetic surfactants which may be so utilized can be non-soap, anionic, nonionic, cationic, zwitteronic or amphoteric in nature.

Low foaming nonionic surfactants are preferred for the low foaming therapeutic toothpastes of the present invention. Where high foaming surfactants are used, an appropriate level of a foam control substance along with a nonionic surfactant is added to the formulation to achieve the low foam interference abrasive "packing" and substantially bubble-free abrasive/tooth surface contact illustrated in FIGS. 3 and 4 of the drawings. These foam control substances are described in detail below.

Suitable surfactants are described in U.S. Pat. Nos. 3,959, 458; 3,937,807; and 4,051,234. Anionic surfactants useful herein include the water soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixture of anionic surfactants can also be employed.

The nonionic surfactants which can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of ethylene oxide condensates of aliphatic alcohols, long chain tertiary amine oxides, long chain tertiary phophine oxides, long chain dialkyl sulfoxides and mixtures of such materials.

The zwitteronic synthetic surfactants useful in the composition of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate.

The cationic surfactants useful in the compositions of the present invention can be broadly defined as quaternary ammonium compounds having one long alkyl chain containing from about 8 to 18 carbon atoms such as lauryl trimethylammonium chloride, cetyl pyridinium chloride, cetyl trimethylammonium bromide; di-isobutylphenoxyethoxyethyl-dimethylbenzylammonium chloride; coconut-alkyltrimethylammonium nitrite; cetyl pyridinium fluoride; etc.

The amphoteric surfactants useful in the present invention can be broadly described as derivatives of aliphatic secondary and tertiary amines in which the aliphatic radical can be straight chain or branched and wherein one of the aliphatic substituents contains from about 8 to 18 carbon atoms and one contains an anionic water-solubilizing group, e.g., carboxylate, sulfonate, sulfate, phosphate, or phosphonate.

HUMECTANT

Another essential component of the low foaming toothpaste composition of the present invention is a humectant. The humectant serves to keep the toothpaste compositions from hardening upon exposure to air. Certain humectants can also impact desirable sweetness or flavor to the toothpaste. The humectant, on a pure humectant basis, generally comprises from between 30% and 70%, preferably from between about 45% and 65%, by weight of the toothpaste compositions herein. (See Examples XI, XII and XIII.)

Suitable humectants for use in this invention include edible polyhydric polyols such as glycerin, sorbitol, xylitol, polyethylene glycol, polypropylene glycol, mannitol, maltitol, etc. Sorbitol is frequently employed as a 70% aqueous solution obtained from SPI Polyols, Inc., New Castle, Del. Mixtures of glycerin and sorbitol are particularly useful in the low foaming toothpastes of the present invention.

In a preferred embodiment of the invention, the humectant is selected from liquid oxyalkylated diols that have a molecular weight in the range between about 200 and 8000. Polyethylene glycols are commercially available under tradenames such as Carbowax 200, 300, 400, 600, 900, 1000, 2000, 4000, 6000, and 8000 from Union Carbide where the number values are approximations at average molecular weight. Polyethylene-propylene glycols are commercially available under tradenames such as Pluracare/ Pluronic L-31 and L-35 from BASF.

In the low foaming therapeutic toothpastes of the present invention, the liquid vehicle may comprise water and humectant, typically in an amount from between about 10% and 90%, by weight of the toothpaste. In translucent low foaming gel toothpastes, where the retractive index is an important consideration, it is preferred to use higher ratios of humectant to water than those used in opaque toothpastes.

FOAM CONTROL AGENT

For these low foaming toothpaste compositions of the invention that contains foam generating surfactants such as anionic and cationic surfactants, it may be necessary to substitute nonionic low foaming surfactants in part or in total and/or add a foam control agent in order to avoid surfactant bubble interference with the abrasive/tooth surface contact and in order to assure abrasive packing of the channeled bristle toothbrushes, both of which features are necessary to achieve CEC and AEC values above about 1.1.

Most toothpaste surfactants generate a controlled level of foam (suds) that remains reasonably stable, eventually breaking down near the end of the toothbrushing cycle. It is this initial bubble formation, at the outset of toothbrushing, that poses the most significant interference threat to abrasive packing in the channeled bristle toothbrushes and to the abrasive/tooth surface interface. In most instances, the toothbrush is not reloaded with toothpaste once brushing starts and it is the distribution of the toothpaste abrasive on the initial "pass" of the bristles over the tooth surfaces that determines the CEC and AEC values of most toothpastes.

Examples of suitable foam control agents for the low foaming toothpastes of the present invention include alcohols such as ethanol, low molecular weight polydimethylsiloxanes such as Silicone, 350, and 1500 from Dow Corning Corporation, Midland, Tex.

Low HLB (Hydrophile-Lipophile-Balance) surfactants such as ARLACEL 186 surfactants, manufactured by ICI Specialty Chemicals, Wilmington, Delaware, when used at approximately 0.1%, will effectively control most foaming in commercial toothpastes and produce abrasive packing and abrasive/tooth surface contact substantially free from bubble interference. Preferred foam control agents for commercial toothpastes include lipophilic oleates and/or laureates with an HLB range from between about 1 and 8.

Although foam control agents can be used effectively to control the foam of various commercial toothpastes, it is preferred to substitute nonionic low foaming surfactants for the sodium lauryl sulfate-type surfactants generally used in most commercial toothpastes. Such substitution is illustrated in Examples I through XIII below.

WATER

Water is another essential element of the toothpastes of this invention. Water employed in the preparation of commercially suitable low foaming, therapeutic toothpastes should preferably be deionized and free of organic impurities. Water comprises from about 10% to 45%, preferably from about 20% to 35%, by weight of the toothpaste compositions herein. These amounts of water include the free water that is added plus that which is introduced with other materials.

ACTIVE THERAPEUTIC INGREDIENTS

Therapeutic ingredients for the treatment of hypersensitivity that can be included in the low foaming toothpastes of the present invention include potassium nitrate, stannous fluoride, zinc chloride and various abrasives that demonstrate a propensity for "tubule" closure during brushing with the low foaming toothpastes of the invention.

The treatment of caries requires a therapeutic substance that functions as a source of fluoride ion. The number of such sources is great and includes those disclosed in U.S. Pat. No. 3,535,421, incorporated herein by reference. Typical materials include: stannous fluoride, potassium fluoride, lithium fluoride, cesium fluoride, ammonium fluoride, aluminum fluoride, capric fluoride, indium fluoride, stannous fluorozirconate, lead fluoride, ferric fluoride, nickel fluoride, paladium fluoride, silver fluoride, zinc fluoride, zirconium fluoride, hexylamine hydrofluoride, laurylamine hydrofluoride, myristylamine hydrofluoride, decanolamine hydrofluoride, octadecanylamine hydrofluoride, myristoxyamine hydrofluoride, diethylamino-ethyloleylamide hydrofluoride, diethanolamino-ethyloleylamide hydrofluoride, diethanolaminopropyl-N'-octadecanylamine dihydrofluoride, 1-ethanol-2-hexadecylimidazoline dihydrofluoride, octoylethanolamine hydrofluoride, octyltrimethylammonium fluoride, dodecyliethyldimethylammonium fluoride, tetraethylammonium fluoride, diaryidmethylamonium fluoride diazoryl-dimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldmethylammonium fluoride, phenoxyethylcetyldimethylammonium fluoride, N,N'-tetramethyl-N,N'-dilaurylethylendiammonium difluoride, N-cetylpyridinium fluoride, N,N-dilaurylmorpholinium fluoride, N-myristyl-N-ethylmorpholinium fluoride, N-(octylaminocarbonylethyl)-N-benzyl-dimethylammonium fluoride, N-(β-hydroxydodecyl)trimethylammonium fluoride, N-phenyl-N-hexadecyldiethylammonium fluoride, N-cyclohexyl-N-octadecyl-dimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethyammonium fluoride, N-(2-(N,N'-dimethyl-aminocarbonyl)-ethyl)-N-dodecyldiethylammonium fluoride, N-carboxymethyl-N-cicoxyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, sodium monofluorophosphete and mixtures thereof. Sodium fluoride is the preferred fluoride source. The amount of the fluoride ion source should be sufficient to provide from about 50 ppm to 3500 ppm, preferably from about 500 ppm to 3000 ppm of fluoride ions.

Anticalculus active ingredients include various pyrophosphate substances. The pyrophosphate salts useful in the present composition include dialkali metal pyrophosphates and mixtures of the dialkali metal and tetraalkali metal pyrophosphate salts. $Na_2H_2P_2O_7$, $Na_2P_2O_7$ and $K_1P_2O_7$ in their unhydrated as well as hydrated forms are the preferred species. The levels of each of these species that preferably are used in the compositions are as follows (all are in the unhydrated form):

| | | |
|---|---|---|
| $Na_2H_2P_2O_7$, | 0.5% | 13.8% |
| $Na_2P_2O_7$ | 0 | 6.0% |
| $K_1P_2O_7$ | 0 | 4.0% |

Preferred $P2O_3^{-4}$ in the present compositions is 1.5% which can be provided solely by $Na_2H_2P_2O_7$ or mixtures of $Na_2H_2P_2O_7$ with either or both of the tetra alkali metal salts. Preferred are binary mixtures of the sodium salts and ternary mixtures of those with the tetra potassium salt. The upper limits on the sodium species are determined by solubility considerations while the tetra potassium level is established for taste reasons.

The pyrophosphate salts are described in more detail in Kirk & Othmer, *Encyclopedia of Chemical Technology*, Second Edition, Volume 15, Interscience Publishers (1968) incorporated herein by reference.

This reference discloses sodium salts including tetrasodium pyrophosphate, disodium dihydrogen pyrophosphate, trisodium hydrogen phosphate and sodium trihydrogen pyrophosphate on the bottom of page 243 and the top of page 244; potassium pyrophosphate on page 249; and diammonium dihydrogen pyrophosphate, triammonium hydrogen phosphate and tetraammonium pyrophosphate on page 249. The reference further discloses condensed phosphoric acids exemplified by pyrophosphoric acid on page 214. The solubilities of sodium pyrophosphates are presented in a diagram at the top of page 243. The reference in total not only discloses a wide range of soluble pyrophosphate sources but also their properties. Bis-biguanide antiplaque agents can also be added to the composition of this invention. Such agents include chlorhexidine (1,6bis [$N^5$-p-chlorophenyl-$N^1$-biguanido]hexane), the soluble and insoluble salts thereof and related materials such as 1,2-bis ($n^5$-p-tri-fluoromethylphenyl-$N^1$-biguanido)ethane are described more fully in Haefels, U.S. Pat. No. 3,923,002, U.S. Pat. No. 3,937,807, Belgian Pat. No. 843,244, and Belgian Pat. No. 844,764. These patents are incorporated herein by reference.

If present, these antiplaque agents generally comprise from about 0% to about 5% by weight of the compositions herein.

Poloxamer polydimethylsiloxane emulsions which function as antiplaque active ingredients available under the trademarks MICRODENT® and ULTRAMULSION® from WhiteHill Manufacturing, Stafford, Tex., are also suitable therapeutic ingredients for the low foaming toothpastes or the present invention.

It is well accepted that hydrogen peroxide and other peroxygen-containing agents are effective in curative and prophylactic treatments with respect to dental plaque, calculus, gingivitis, mouth odor, tooth stains, mucosal infections, and the like.

Many oral care products have been formulated which include a peroxy compound, and more recently oral care products have been developed which include a peroxy compound having improved stability. References that describe peroxy-containing toothpastes include: U.S. Pat. Nos. 2,275,979; 3,577,521; 3,657,413; 3,885,028; 3,886,265; 4,226,851; 4,302,441; 4,405,599; 4,426,108; 4,431,631; 4,521,403; 4,522,805; 4,528,180; 4,567,036; 4,592,487; 4,592,488; 4,592,489; 4,687,663; 4,812,308; 4,837,008; 4,839,152; 4,849,213; 4,867,988; 4,891,211; 4,897,258; 4,925,655; 4,971,782; 4,980,152; 4,988,450; 5,000,941; 5,041,280; 5,085,853; 5,256,402; and the like, incorporated herein by reference.

OPTIONAL INGREDIENTS

Low foaming therapeutic toothpastes, creams, gels and powders of the invention typically also contain a natural or synthetic thickener or gelling agent in proportions of about 0.1% to about 10%, preferably about 0.5% to about 5%, by weight. Suitable organic thickeners include sodium carboxymethyl cellulose, gum tragacanth, starch, carrageenan, polyvinylpyrrolidone, hydroxyethylpropyl cellulose, hydroxybutylmethyl cellulose, hydroxypropylmethyl cellulose or hydroxyethyl cellulose, and are usually used in concentrations of 0.1% to 2.0%. Inorganic thickeners such as hydrated silicas may also be used at levels of about 0.5% to 10%.

Suitable flavoring and sweetening agents may also be employed in the dentifrices of the invention. Examples of suitable flavorants include the flavoring oils, for example, oils of spearmint, peppermint, wintergreen, sassafras, clove, sage, eucalyptus, marjoram, cinnamon, lemon and orange, as well as methylsalicylate. Suitable sweeteners include sodium cyclamate, perillartine, saccharin, sodium saccharin and ammoniated glycyrrhizin (e.g. its monoammonium salt), and the like. Suitably, the flavoring and sweetening agent together comprise from about 0.01% to 5% or more by weight of the dentifrice. Preferably, the amount of flavoring oil is above 0.3%, e.g. 0% to 1.2%.

The pH of the compositions herein is in the range of 6.0 to 10.0, preferably from 7.3 to 9.0. The pH is preferably achieved through a proper balancing of the pyrophosphate salts or by the addition of an alkaline or acidic agent.

EXAMPLES

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

Example 1

The following is a low foaming therapeutic toothpaste representative of the present invention.

| Component | % |
|---|---|
| Distilled Water | 16.484 |
| Sorbitol (70% Aqueous Solution) | 49.565 |
| Sodium Saccharin | 0.300 |
| Dye Solution | 0.350 |
| Precipitated Silica | 20.000 |
| Sodium Fluoride | 0.243 |
| Flavor | 1.330 |
| Low foaming nonionic poloxamer surfactant/ foam control Arlacel 186 (at 0.1%) mixture | 2.000 |
| Carbopol 940* | 0.180 |
| Xanthan Gum | 0.600 |
| $Na_4P_2O_7$ | 2.400 |
| $Na_2H_2P_2O_7$ | 1.190 |
| $K_4P_2O_7$ (61.5 Aqueous Solution) | 3.360 |
| | 100.000 |

*Carboxy vinyl polymer offered by H. F. Goodrich Company.

The above composition is made by combining the water and part of the sorbitol in an agitated mixture and heating this mixture to 140° F. The $Na_2H_2P_2O_7$, $Na_4P_2O_7$, saccharin, sodium fluoride and precipitated silica are then added in order and the total mixture was mixed for from 5 to 10 minutes. The flavor, dye and the poloxamer surfactant are then added. In a separate vessel the remainder of the sorbitol, the Carbopol and the Xanthan gum are slurried together and then added to the main mix tank. The complete batch is mixed for about one-half hour and subsequently milled and deaerated.

Example 2

The following is another representative toothpaste of the present invention.

| Component | % |
|---|---|
| Sorbitol (70% Aqueous Solution) | 50.723 |
| Distilled Water | 16.484 |
| Sodium Saccharin | 0.300 |
| Dye Solution | 0.350 |
| Precipitated Silica | 20.000 |
| Sodium Fluoride | 0.243 |
| Flavor | 1.330 |
| Low foaming nonionic Pluronic surfactant/ Arlacel 186 (at 0.1%) mixture | 5.000 |
| Carbopol 940S | 0.180 |
| Xanthan Gum | 0.600 |
| $Na_4P_1O_7$ | 3.400 |
| $Na_2H_2P_2O_7$ | 100.000 |

Both the composition of Example I and that of Example II are effective in reducing calculus and possess acceptable cosmetic properties.

Examples 3–6

The following dentifrice compositions are representative of the present invention.

| | Weight % | | | |
|---|---|---|---|---|
| Component | Ex. 3 | Ex. 4 | Ex. 5 | Ex. 6 |
| Water | 12.500 | 12.500 | 12.500 | 12.500 |
| Sorbitol (70% Solution) | 47.891 | 45.727 | 43.437 | 41.328 |
| Glycerin | 10.198 | 10.198 | 10.198 | 10.000 |
| PEG-12 | — | — | — | — |
| Titanium Dioxide | 2.525 | 0.525 | 0.525 | 0.525 |
| Silica | 20.000 | 20.000 | 20.000 | 20.000 |
| Na Carboxymethyl Cellulose | 1.010 | 1.050 | 1.050 | 1.000 |
| Na Carrageenan | — | — | — | 0.350 |
| Magnesium Alumina Silicate | 0.408 | 0.408 | 0.408 | — |
| Hydroxyethyl Cellulose | — | — | — | — |
| Nonionic low foaming poloxamer with 0.1% Arlacel 186 | 4.000 | 4.000 | 4.000 | 4.000 |
| Na Gluconate | 0.632 | 2.395 | 4.750 | 3.314 |
| Stannous Fluoride | 0.454 | 0.454 | 0.454 | 0.454 |
| Stannous Chloride Dihydrate | — | 1.141 | 1.141 | 2.198 |
| Stannous Pyrophosphate | 1.040 | — | — | — |
| Na Saccharin | 0.700 | 0.200 | 0.200 | 0.230 |
| Flavor | 0.831 | 0.851 | 0.851 | 1.000 |
| FD&C Blue #1 (1% Solution) | 0.051 | 0.051 | 0.051 | 0.051 |
| Na Hydroxide (50% Solution) | 0.200 | 0.300 | 0.385 | 0.850 |
| pH | 4.5 | 4.5 | 4.5 | 4.5 |

Examples 7–10

The following dentifrice compositions are representative of the present invention.

| | Weight % | | | |
|---|---|---|---|---|
| Component | Ex. 7 | Ex. 8 | Ex. 9 | Ex. 10 |
| Water | 12.500 | 16.500 | 12.500 | 12.500 |
| Sorbitol (70% Solution) | 45.712 | 42.135 | 43.730 | 48.708 |
| Glycerin | 10.000 | 10.000 | 10.000 | 10.000 |
| PEG-12 | — | 3.000 | — | — |
| Titanium Dioxide | 0.525 | 0.525 | 0.515 | 0.325 |
| Silica | 20.000 | 20.000 | 20.000 | 20.000 |
| Na Carboxymethyl Cellulose | 1.000 | — | 1.000 | 0.900 |
| Na Carrageenan | 0.330 | 0.450 | 0.310 | 0.350 |
| Magnesium Alumina Silicate | — | — | — | — |
| Hydroxyethyl Cellulose | — | 0.400 | — | — |
| Low Foaming Pluronic F127/ Arlacel 186 mixture | 4.000 | 4.000 | 4.000 | 4.000 |
| Na Gluconate | 2.082 | 2.395 | 2.395 | 2.082 |
| Stannous Fluoride | 0.454 | 0.454 | 0.454 | 0.908 |
| Stannous Chloride Dihydrate | 1.500 | 1.141 | 1.141 | 0.346 |
| Stannous Pyrophosphate | — | — | — | — |
| Na Saccharin | 0.230 | 0.230 | 0.230 | 0.230 |
| Flavor | 1.000 | 1.000 | 1.000 | 1.000 |
| FD&C Blue #1 (1% Solution) | 0.051 | 0.050 | 0.051 | 0.051 |
| Na Hydroxide (50% Solution) | 0.600 | 0.600 | 0.600 | 0.700 |
| pH | 4.5 | 4.5 | 4.5 | 4.5 |

PROCEDURE FOR MAKING LOW FOAMING THERAPEUTIC DENTIFRICE

In preparing the dentifrice formulations for Examples 3 to 10, sorbitol and one half of the water are added to the mix tank and heating to 77° C. initiated. Saccharin, titanium dioxide, and silica may be added to the mixture during this heating period. Sufficient agitation is maintained to prevent the settling of the insoluble components. The glycerin is added to a separate vessel and is also heated to 77° C. When both the solutions have attained the required temperature, the carboxymethyl cellulose (CMC) and carrageenan are blended together and slowly added to the glycerin under vigorous agitation. When the CMC and carrageenan are sufficiently dispersed in the glycerin, this mixture is added to the sorbitol/water mixture. The resulting mixture is then blended for a sufficient period of time to allow complete hydration of the binders (about 15 minutes). When the paste is of acceptable texture, the flavor, Pluronic F127/Arlacel 186 mixture and color are added. One half of the remaining water is then added to a separate mix tank and allowed to heat to 77° C. After the water attains the necessary temperature, the sodium gluconate is added under medium agitation and allowed to dissolve completely. The stannous chloride dihydrate is then added to the gluconate solution and also allowed to dissolve. This mixture is added to the main mix. The stannous fluoride is added to the remaining water (also at 77° C.) and the resulting solution is added to the main mix and allowed to blend thoroughly before final pH adjustment with sodium hydroxide. The completed paste is agitated for approximately 20 minutes before being milled and deaerated.

It is particularly preferred to incorporate the following ingredients: sodium/alkali metal pyrophosphate-containing, calculus inhibiting ingredients in the low foaming toothpastes or dental creams of the invention.

Example 11

Toothpastes or Dental Creams

| | Amounts, Percent by Weight (Unless Otherwise Indicated) | |
|---|---|---|
| Ingredient | Broad Range | Preferred Range |
| Sodium Bicarbonate | 20.00 to 65.00 | 30.00 to 60.00 |
| Pyrophosphate Salt | 2.50 to 13.00 | 2.50 to 3.00 |
| Humectant | 3.00 to 60.00 | 10.00 to 35.00 |
| Organic Thickener | 1.00 to 2.00 | 0.30 to 1.50 |
| Inorganic Thickener | 9.00 to 10.00 | 0.00 to 5.00 |
| Nonionic Low Foam Surfactant | 0.05 to 5.00 | 0.10 to 1.00 |
| Water Insoluble Abrasive | 0.00 to 50.00 | 0.00 to 20.00 |

-continued

Toothpastes or Dental Creams

| Ingredient | Amounts, Percent by Weight (Unless Otherwise Indicated) | |
|---|---|---|
| | Broad Range | Preferred Range |
| Sweetener | 0.00 to 10.00 | 0.30 to 2.00 |
| Fluoridating Agent as fluoride ion | 23.00 to 3000 ppm | 850 to 1500 ppm |
| Flavoring Agent | 0.01 to 5.00 | 0.30 to 2.00 |
| Water | 3.00 to 60.00 | 5.00 to 35.00 |

In another particularly preferred embodiment, the following ingredients are incorporated in sodium bicarbonate/alkali metal pyrophosphate-containing, calculus inhibiting low foaming dental gels.

Example 12

Dental Gels

| Ingredient | Amounts, Percent by Weight (Unless Otherwise Indicated) | |
|---|---|---|
| | Broad Range | Preferred Range |
| Sodium Bicarbonate | 20.00 to 60.00 | 20.00 to 40.00 |
| Pyrophosphate Salt | 2.50 to 15.00 | 2.50 to 5.00 |
| Humectant | 10.00 to 60.00 | 10.00 to 50.00 |
| Organic Thickener | 0.10 to 2.00 | 0.30 to 1.50 |
| Inorganic Thickener | 0.00 to 10.00 | 3.00 to 8.00 |
| Nonionic Low Foam Surfactant | 0.00 to 10.00 | 0.30 to 1.00 |
| Water Insoluble Abrasive | 0.00 to 50.00 | 0.00 to 20.00 |
| Sweetener | 0.00 to 10.00 | 0.30 to 2.00 |
| Fluoridating Agent as fluoride ion | 15.00 to 5000 ppm | 850 to 1500 ppm |
| Flavoring Agent | 0.01 to 5.00 | 0.30 to 2.00 |
| Water | 3.00 to 30.00 | 5.00 to 20.00 |

In another preferred embodiment of the invention, anti-calculus low foaming tooth powders contain the following ingredients.

Example 13

Toothpaste Powders

| Ingredient | Amounts, Percent by weight (Unless Otherwise Indicated) | |
|---|---|---|
| | Broad Range | Preferred Range |
| Sodium Bicarbonate | 20.00 to 95.00 | 50.00 to 95.00 |
| Pyrophosphate Salt | 2.50 to 13.00 | 2.50 to 5.00 |
| Nonionic Low Foam Surfactant | 0.00 to 10.00 | 0.00 to 2.00 |
| Water Insoluble Abrasive | 0.00 to 95.00 | 0.00 to 50.00 |
| Sweetener | 0.00 to 10.00 | 0.30 to 2.00 |
| Fluoridating Agent as fluoride ion | 25.00 to 3000 ppm | 850 to 1500 ppm |
| Flavoring Agent | 0.01 to 5.00 | 0.30 to 2.00 |
| Anti-caking Agent | 0.00 to 5.00 | 0.05 to 0.20 |

In addition to the levels and combinations of ingredients shown in these examples, others can be used which are consistent with the invention disclosed and claimed herein.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A low foaming, therapeutic toothpaste comprising the following ingredients:
   (a) from about 1% to 90% by weight of one or more abrasives with particle sizes ranging from about 3 to 25 microns;
   (b) from about 30% to 70% by weight of one or more humectants;
   (c) from about 10% to 45% water;
   (d) a foam controlled surfactant; and
   (e) one or more active therapeutic agents selected from the group consisting of anti-plaque, anti-tartar, anti-gingivitis, anti-caries, anti-hypersensitivity treatment substances, and mixtures thereof.

2. A low foaming therapeutic toothpaste according to claim 1, wherein the therapeutic substance is selected from the group consisting of fluoride ion sources, pyrophosphate anticalculus agents, bis-biguanide antiplaque agents, peroxygen agents, and mixtures thereof.

3. A low foaming therapeutic toothpaste according to claim 1, wherein the hypersensitivity treatment substance is selected from the group consisting of potassium nitrate, stannous fluoride, and zinc chloride.

4. A low foaming therapeutic toothpaste according to claim 1, wherein the water is present at from about 20% to 35% by weight of the toothpaste composition.

5. A low foaming therapeutic toothpaste according to claim 1, wherein the humectant is present at from about 45% to 65% by weight of the toothpaste composition.

6. A low foaming therapeutic toothpaste according to claim 1, wherein the water and the humectant combined represent from about 10% to 90% by weight of the toothpaste composition.

7. A low foaming therapeutic toothpaste according to claim 1, further comprising additional ingredients selected from natural and synthetic thickeners or gelling agents at from about 0.1% to 10% by weight.

8. A low foaming therapeutic toothpaste according to claim 1, further comprising flavoring and/or sweetening agents at from about 0.01% to 5% by weight.

9. A method of treating the oral cavity comprising brushing with a low foam toothpaste comprising the following ingredients:
   (a) from about 1% to 90% by weight of one or more abrasives with particle sizes ranging from about 3 to 25 microns;
   (b) from about 30% to 70% by weight of one or more humectants;
   (c) from about 10% to 45% water;
   (d) a foam controlled surfactant; and
   (e) one or more active therapeutic agents selected from the group consisting of anti-plaque, anti-tartar, anti-gingivitis, anti-caries, anti-hypersensitivity treatment substances, and mixtures thereof.

10. A method according to claim 9, wherein the wherein the therapeutic substance is selected from the group consisting of fluoride ion sources, pyrophosphate anticalculus agents, bis-biguanide antiplaque agents, peroxygen agents, and mixtures thereof.

11. A method for treating tooth hypersensitivity comprising regularly brushing sensitive teeth areas with a low foaming, therapeutic toothpaste comprising the following ingredients:

(a) from about 1% to 90% by weight of one or more abrasives with particle sizes ranging from about 3 to 25 microns;
(b) from about 30% to 70% by weight of one or more humectants;
(c) from about 10% to 45% water;
(d) a foam controlled surfactant; and
(e) one or more active anti-hypersensitivity treatment substances selected from the group consisting of potassium nitrate, stannous fluoride, zinc chloride, tubule closing abrasive compounds, and mixtures thereof.

* * * * *